(12) United States Patent
Bruce

(10) Patent No.: US 6,654,118 B2
(45) Date of Patent: Nov. 25, 2003

(54) METHOD AND APPARATUS FOR OBTAINING MOLECULAR DATA FROM A PHARMACEUTICAL SPECIMEN

(75) Inventor: Richard David Bruce, Rydal, PA (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 10/339,584

(22) Filed: Jan. 9, 2003

(65) Prior Publication Data

US 2003/0147066 A1 Aug. 7, 2003

Related U.S. Application Data

(60) Provisional application No. 60/354,252, filed on Feb. 4, 2002.

(51) Int. Cl.[7] ............................. G01J 3/44; G01J 3/06
(52) U.S. Cl. ......................... 356/301; 356/309; 356/73
(58) Field of Search ........................... 356/309, 301, 356/237.2, 237.3, 399, 400, 401, 73; 250/559.45, 559.99, 559.16, 225

(56) References Cited

U.S. PATENT DOCUMENTS

| | | | | |
|---|---|---|---|---|
| 4,407,008 A | * | 9/1983 | Schmidt et al. | 358/93 |
| 5,706,083 A | * | 1/1998 | Iida et al. | 356/328 |
| 5,715,052 A | * | 2/1998 | Fujino et al. | 356/237 |
| 5,811,804 A | * | 9/1998 | Van Blitterswijk et al. | 250/311 |
| 6,067,154 A | * | 5/2000 | Hossain et al. | 356/237.2 |
| 6,069,690 A | * | 5/2000 | Xu et al. | 356/73 |
| 6,288,782 B1 | * | 9/2001 | Worster et al. | 356/394 |

FOREIGN PATENT DOCUMENTS

| | | | | |
|---|---|---|---|---|
| FR | 2596863 A1 | * | 4/1986 | G01N/23/00 |

* cited by examiner

Primary Examiner—Frank G. Font
Assistant Examiner—Layla Lauchman

(57) ABSTRACT

This invention relates to a method and apparatus for the analysis of pharmaceutical specimens by nondestructively obtaining the molecular data for a chemical component on the surface or within the matrix of a pharmaceutical specimen.

24 Claims, 2 Drawing Sheets

METHOD AND APPARATUS FOR OBTAINING MOLECULAR DATA FROM A PHARMACEUTICAL SPECIMEN

CROSS REFERENCE TO RELATED APPLICATION

This application is based on U.S. Provisional Application Ser. No. 60/354,252, filed filed Feb. 4, 2002, which is hereby incorporated by reference.

FIELD OF THE INVENTION

This invention relates to a method and apparatus for the analysis of pharmaceutical specimens. More particularly, to a method and apparatus for nondestructively obtaining the molecular data for a chemical component on the surface of or within the matrix of a pharmaceutical specimen.

BACKGROUND OF THE INVENTION

For analyzing a pharmaceutical specimen, it would be useful to be able to simultaneously determine the position for a chemical component on the surface or within the matrix of the specimen and its corresponding molecular data. Such position-related data could be used as the baseline profile for the pharmaceutical specimen at a given time and could allow analysis at a later time to determine changes of the chemical composition of the specimen. Information gained from analysis of a chemical profile could aid a pharmaceutical formulator in identifying any needed refinements to the formulation or manufacturing process. Additionally, it is desirable to examine the pharmaceutical specimen before and after selected manufacturing steps and at various timepoints during a stability study. Therefore, a nondestructive and reproducible analysis method is needed.

Some of the currently used analysis methods provide information on either the physical structure or elemental components of surface defects. Commonly used nondestructive structural analysis techniques include light microscopy (LM), infrared (IR) absorption spectroscopy and scanning electron microscopy (SEM).

LM is a comparatively simple technique that provides a relatively low resolution image of a specimen and can be used to detect surface particles of about 0.5 microns in diameter. LM enables locating a small area on the surface of a pharmaceutical specimen from which molecular data may obtained from the surface or from within the matrix of the specimen. LM has limited use in a pharmaceutical application, though, because it is not possible to find and focus on a single submicron chemical component. Manually searching for a small area using a microscope is extremely difficult, if not impossible for a smaller target within the region, with submicron targets simply not visible by light microscopy.

The technique of IR absorption spectroscopy is a commonly-used nondestructive technique for obtaining molecular identification of materials. IR absorption spectroscopy involves detecting molecular vibrations, or vibrations characteristic of atoms which are bonded together. Incident radiation which has the same frequency as a molecular vibration in the material is absorbed. The result of the measurement is typically a plot of transmitted radiation intensity versus wavenumber (reciprocal of wavelength) of the radiation, showing many transmission dips corresponding to vibrational mode frequencies. Coupling between vibrations involving different parts of a molecule results in a complex spectrum which provides a distinctive signature for the particular chemical compound and phase being measured. However, the water peak typically present using the IR technique limits the usefulness of IR in obtaining molecular data from a pharmaceutical specimen. Another problem with the IR technique is the spot size of the incident beam. Wavelengths of the vibrations used for identification of most chemical compounds are in the mid-infrared range, from approximately 2 microns to 25 microns. Because the wavelength of the incident radiation must match that of the vibrations to obtain an absorption spectrum, the incident radiation used in IR absorption measurements is also in the wavelength range of 2 microns to 25 microns. The spot size of a beam of radiation is related to its wavelength such that the lower limit of the spot size is on the order of the wavelength. Therefore, the area illuminated by the incident radiation in an IR absorption measurement and the area from which the resulting absorption signal is collected can be on the order of 25 microns in diameter. Because many of the chemical components of a pharmaceutical specimen are of submicron size, this illumination area is much too large for isolation of a particular element for analysis. To be useful for analysis of submicron-sized particles, an illumination area having a diameter of less than one micron is needed. Accordingly, the use of the typical infrared means of detection, IR absorption spectroscopy, is also limited in a pharmaceutical application because the water peak can obscure or hide spectra of interest and the area from which molecular data is collected is not small enough.

In SEM, a beam of primary electrons is directed at the surface of a specimen and emitted secondary electrons are detected in order to form a topographical image of the surface at a higher resolution than LM. Pharmaceutically interesting SEM subjects are nearly always nonconductive to the SEM beam, though, unless conductively coated. The conductive coating provides a source of secondary electrons that are excited by the primary SEM beam and subsequently detected to provide the surface image. The conductive coating material, however, obscures the surface of a pharmaceutical specimen and prevents obtaining molecular data from the specimen's surface. The coating also prevents obtaining molecular data from within the matrix of the specimen. Additionally, SEM requires that the specimen be placed in a vacuum chamber. The vacuum chamber is maintained at a negative pressure of up to $10^{-5}$ Torr to remove any water vapor and, thus, reduce distortion. As a result of the vacuum, however, the specimen becomes dehydrated and cannot be used for analysis again at a later date. Standard SEM is therefore only useful for topographic analysis, with limited usefulness for reproducibly obtaining molecular data from the surface or within the matrix of a pharmaceutical specimen.

Another topographic analysis technique is scanning probe microscopy (SPM). SPM comprises a family of techniques in which a probe is held extremely close to a surface and scanned with high resolution and accuracy (tenths of nanometers). Some interaction between the probe and the surface is then measured. In the case of scanning tunneling microscopy, for example, tunneling current is measured. Another commonly used SPM technique in structural characterization is atomic force microscopy (AFM), in which the force between the probe and surface is measured. Typical applications include measurement of roughness, pinholes and other topographical features on a specimen. SPM techniques and applications have limited usefulness, though, for obtaining molecular data from the surface or within the matrix of a pharmaceutical specimen.

Other nondestructive techniques commonly used for elemental analysis include Auger emission spectroscopy (AES) and X-ray fluorescence spectroscopy (XRF). Like SEM techniques, AES techniques involve directing a beam of primary electrons at the specimen. Instead of forming an image using detected secondary electrons emitted by atoms on the upper surface, AES techniques measure the energy levels of the emitted electrons to determine elemental components of surface structures. In XRF techniques, a beam of primary X-rays is directed at the surface and the energy levels (or corresponding wavelengths) of resultant secondary X-rays emitted by atoms of elements on and just under the surface are measured. Atoms of elements in target materials emit secondary X-rays with uniquely characteristic energy levels (or corresponding wavelengths). Thus the elemental components of materials on and just under the surface may be determined from the measured energy levels (or wavelengths) of emitted secondary X-rays. The techniques for elemental analysis also have limited usefulness for obtaining the type of detailed chemical component data (i.e., other than elemental data) needed for pharmaceutical applications. For example, a technique such as AES or XRF might identify the presence of a chemical element on a surface, but would not be able to determine the molecular data for chemical components in a subsurface layer having a different chemical composition. Knowledge of the actual chemical components present on or in a surface layer or within the matrix of a pharmaceutical specimen at a variety of time-points can be extremely valuable, enabling one skilled in the art to profile a pharmaceutical dosage form at certain points in the manufacturing process or of its stability over time.

U.S. Pat.No. 6,067,154 refers to an apparatus and method related to the field of semiconductor wafer fabrication for finding manufacturing defects within a semiconductor topography and obtaining molecular characterization of such defects using inelastic scattering of incident monochromatic radiation.

U.S. Pat. No. 4,407,008 refers to an apparatus and method related to analysis using light-induced SEM to permit nondestructive identification of specimen specific parameters and their two-dimensional distribution by detection of the subsequent excitation radiation emitted by the specimen using a variety of detection apparatus.

The currently available techniques are useful for surface and elemental analysis, but no method is currently capable of nondestructively providing molecular data for chemical components on or in a surface layer or within the matrix of a pharmaceutical specimen. Due to the limitations of current analytical technology, there is no currently available apparatus that has the capability of providing a submicron image of the specimen, molecular data for surface and subsurface chemical components at different times for a single specimen or of being used in a variety of pharmaceutical applications and environments including, but not limited to, use as an in-process control tool in a pharmaceutical manufacturing environment and use for stability study testing in a pharmaceutical laboratory environment.

It would, be advantageous to provide a method and apparatus for obtaining molecular data on or in a surface layer or within the matrix of a pharmaceutical specimen. It would also be advantageous to provide a method and apparatus for nondestructively obtaining submicron molecular data at different times on or in a surface layer or within the matrix of a single pharmaceutical specimen. It would further be advantageous to provide a method and apparatus for nondestructively obtaining submicron molecular data at different times on or in a surface layer or within the matrix of a single pharmaceutical specimen and for use in a variety of pharmaceutical applications and environments.

SUMMARY OF THE INVENTION

Broadly speaking, the apparatus of the present invention is a system comprising an imaging apparatus, a signal producing apparatus, a detecting apparatus and a mapping apparatus, whereby the molecular data for a chemical component of a pharmaceutical specimen is obtained. The imaging apparatus provides an image of the specimen. The signal producing and detecting apparatus comprise a plurality of incident radiation sources and a plurality of detectors to detect the radiation scattered from the specimen. The mapping apparatus provides a position on or within the matrix of the specimen from which the molecular data is to be obtained.

The method of the present invention comprises the steps of producing an image of a pharmaceutical specimen, using the image to identify and select a position on or within the matrix of the specimen, aligning a plurality of incident radiation sources at the selected position and using a plurality of detection apparatus to detect the intensity and frequency of radiation scattered from the position, thereby obtaining the molecular composition therefrom.

While the invention is susceptible to various modifications and alternative forms, specific embodiments thereof are shown by way of example in the drawings and will herein be described in detail. It should be understood, however, that the drawings and detailed description herein are not intended to limit the invention to the particular form disclosed. On the contrary, the intention is to cover all modifications, equivalents and alternatives falling within the spirit and scope of disclosure and claims of the present invention.

DETAILED DESCRIPTION OF THE INVENTION

Figure 1:
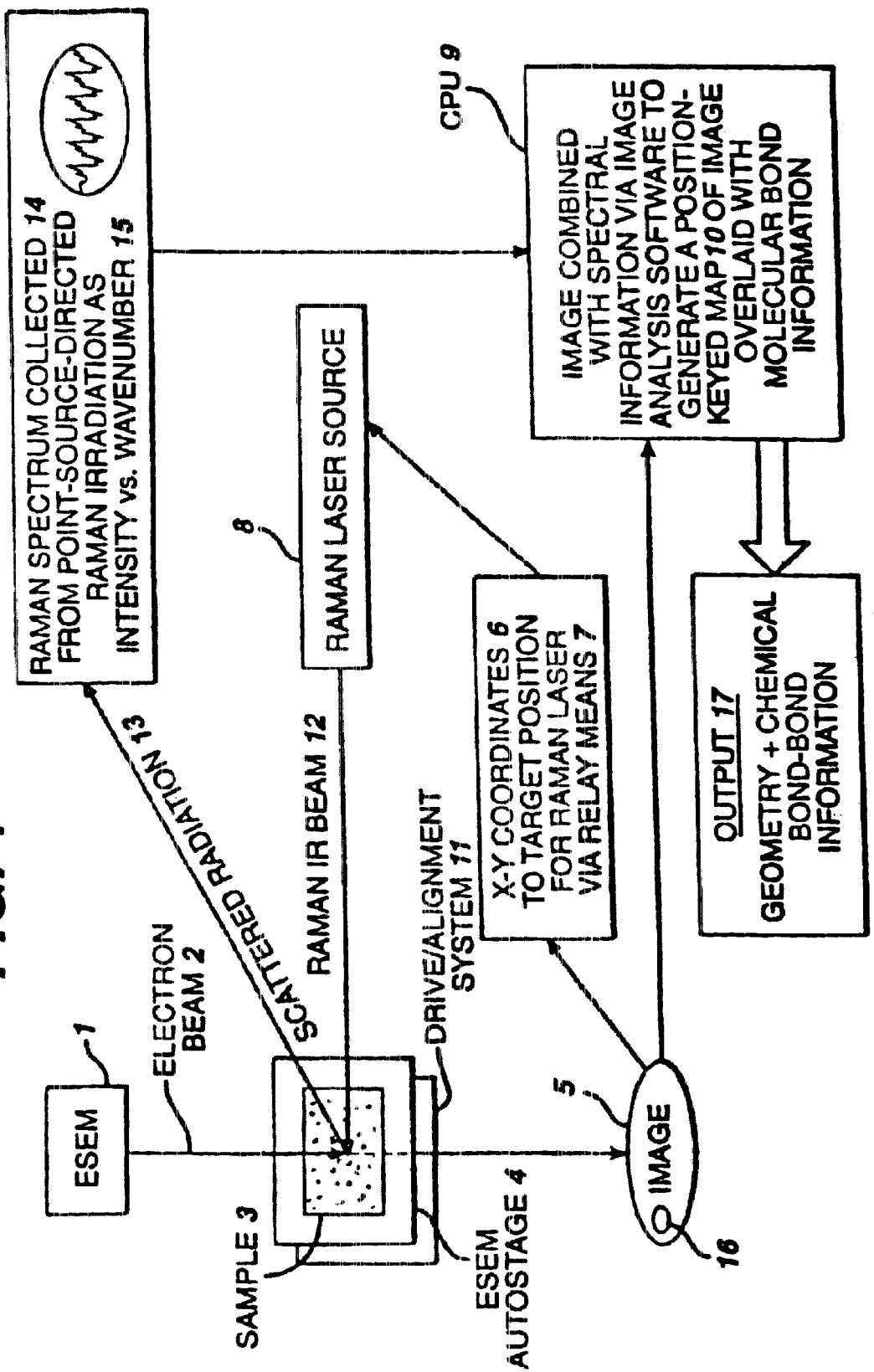
FIG. 1 is a side elevation view of an embodiment of the apparatus described herein.

In an embodiment of the method and apparatus of the present invention, the imaging apparatus comprises an Environmental Scanning Electron Microscope (ESEM) for producing an image of a pharmaceutical specimen and an ESEM autostage on which the specimen is reproducibly placed.

The use of an ESEM for creating an image of the surface of a pharmaceutical specimen is a minimally invasive technique, producing little or no change in the specimen's molecular state. An image of the pharmaceutical specimen is generated by scanning the specimen using radiation from the ESEM. The ESEM provides a first beam of incident radiation directed at the specimen. The ESEM beam is raster-scanned over the specimen's surface. Raster-scanning is defined as a pre-determined pattern of scanning lines that provides substantially uniform coverage of an area. This scanning process is very similar to electron-beam scanning in an ordinary television set, where the result is seen as closely spaced parallel lines. The incident ESEM beam produces a first beam of scattered radiation that results from the interaction of the incident ESEM beam with the specimen's surface. The scattered ESEM beam is then detected by the ESEM to provide a comprehensive, detailed, sub-micron image. The image of the specimen may be stored by the mapping apparatus and then used to reproducibly align the signal producing apparatus at specific positions on a particular specimen for obtaining molecular data at a various times. Since the incident ESEM beam is raster-scanned and does not remain on a fixed location of the specimen, the change in the specimen's molecular state as a result of producing the ESEM image is minimized. The incident ESEM beam interacts with the specimen's surface to produce vibrational radiation in the form of heat. Such vibrational radiation may be filtered or canceled out as baseline radiation using means known to those skilled in the art.

Embodiments of the present invention include an apparatus wherein the incident ESEM beam is alternately turned on and off during analysis. Embodiments also include an apparatus wherein the incident ESEM beam is used dynamically with the signal producing apparatus to concurrently obtain both the ESEM image and the molecular data from a position on or within the specimen. The dynamic use of the incident ESEM beam simultaneously with the signal producing apparatus may be accomplished by means known to those skilled in the art.

The size of the ESEM image may also be varied depending on the size of the area to be scanned. The size of the scanned area depends on the field of view required for the analysis, as determined by the size of the specimen, the size of the chemical components in or on a pharmaceutical composition about which molecular data is sought and the number of incident radiation beam sources being used.

Embodiments of the present invention include an ESEM autostage whereby the specimen may be reproducibly placed on the autostage. Such placement enables collecting molecular data from particular position in or on a specimen over a period of time target and is provided by a placement apparatus incorporated into the autostage. The contemplated placement apparatus allows a specimen sample to be removed after initial analysis and to be replaced at a later time to obtain additional data from a plurality of mapped positions. The placement apparatus includes, and is not limited to, a sample plate on which a specimen is fixedly attached and a sample plate alignment apparatus used for reproducibly placing the sample plate on the autostage. The sample plate alignment apparatus includes, and is not limited to, alignment pins fixed between the sample plate and the autostage or equivalents thereof or gridlines marked onto or debossed into the autostage or equivalents thereof.

In an embodiment of the method and apparatus of the present invention, the signal producing apparatus comprises a plurality of incident radiation beam sources for producing a scattered radiation signal from a position on or within the specimen.

The plurality of incident radiation beam sources includes at least one source of incident radiation selected from a first, second and third incident radiation source.

The plurality of incident radiation sources may be simultaneously aligned with a mapped position targeted using a computer system.

Embodiments of the present invention include a Raman spectroscopy system as the first incident radiation source. The second incident radiation source may be selected from an additional Raman spectroscopy system.

In an embodiment of the method and apparatus of the present invention, the detecting apparatus comprises a plurality of detection apparatus for detecting the scattered radiation from the position as molecular data.

The plurality of detection apparatus includes at least one detection apparatus selected from a first, second and third detection apparatus.

Embodiments of the present invention include a Raman spectroscopy system as the first detection apparatus. The second detection apparatus may be selected from an additional Raman spectroscopy system. The third means of detection may be selected from an energy dispersive X-ray (EDX) system. EDX can be added for elemental anaylsis, when it is useful to determine the elemental composition of a specimen.

The phrase "Raman spectroscopy system," as used herein, refers to any measurement of intensity and frequency of scattered radiation which is used to obtain molecular data from a specimen. In a Raman spectroscopy system, a monochromatic radiation beam from a laser is incident upon a sample to be analyzed and radiation which is scattered by molecular vibrations is detected. Most of the radiation is elastically scattered, so that it undergoes no change in energy or frequency during the scattering process. If molecular vibrations exist which change the polarizability of a molecule, however, a small fraction of the radiation will be inelastically scattered. Such vibrations are said to be "Raman active". The scattered radiation is obtained using a monochromator and detector. The intensity of the scattered radiation is plotted against wavelength number and comprises a large peak at the wavenumber of the incident radiation and a group of small peaks on either side of the large peak, both at higher and lower wavenumbers. The difference between the wavenumber of a Raman peak and that of the incident radiation corresponds to the frequency of the associated vibrational mode. As a result, similar to other spectroscopy means, such as IR absorption spectroscopy, a distinctive signature for a given chemical component results. Raman spectroscopy, however, has the feature that the frequency of the incident radiation does not need to match that of the vibrational modes being detected. Since it is the change in frequency of the scattered radiation that is measured, the incident laser radiation can be at a much higher frequency than that of the vibrational modes. This higher frequency, shorter wavelength radiation can be focused to small spot sizes on the sample being analyzed.

As a result, the use of a Raman spectroscopy system enables sub-micron molecular analysis comporting with the detail and accuracy provided by the ESEM image, thus avoiding the problems described above with other detection means known to those skilled in the art such as, but no limited to, light microscopy, SEM and IR.

Embodiments of the present invention include a method and apparatus wherein, preferably, the Raman spectroscopy system is in the Raman microprobe configuration. In such a configuration, the incident Raman radiation beam is focused to a spot size of approximately 1 micron and, thereby, collects scattered Raman radiation from the immediate vicinity of the radiated spot. In this way, a very small area of a specimen may be analyzed. The depth to which the specimen position is analyzed depends on the penetration depth of the incident Raman beam, which is in turn dependent on the extent to which the incident Raman beam is absorbed by the sample. Because absorption depends on the energy of the incident radiation, with higher-energy radiation absorbed more strongly, the penetration depth of the radiation may be changed by changing its energy.

Therefore, analysis of positions on or in a pharmaceutical specimen may be enhanced when using a Raman spectroscopy system by variation of the energy of the incident Raman beam. For example, analysis may be restricted to the specimen surface for examination of surface chemical components or performed at an increased depth to examine chemical components which are within the matrix of the specimen.

In an embodiment of the method and apparatus of the present invention, the mapping apparatus comprises imaging software for mapping and storing a position location and matching molecular data with the position and an integrated system for aligning the signal producing apparatus with the position location on the ESEM image.

As the initial molecular data from a position on or within the pharmaceutical specimen is obtained, the imaging software maps and stores the position location and the corresponding molecular data for a particular ESEM image. Such software also allows a position map and a selected ESEM image to be imported and correlated with position locations for subsequent analysis of an actual specimen. The subsequent molecular data would also be stored and available for comparison.

The integrated system for aligning the signal producing apparatus with the positions mapped for an ESEM image is a computer system connected to and in communication with the signal producing apparatus. The computer system controls the position and alignment of the plurality of incident radiation sources for any specific mapped position and communicates these positions to the signal producing apparatus, moving the signal producing apparatus such that the selected position for the specimen is aligned with the signal producing apparatus.

The integrated system may also include software which enables simultaneous specimen scanning with an incident ESEM beam to produce the ESEM image and scanning with an incident Raman beam to obtain molecular data. In this way, regions of interest may be detected on an unmapped specimen using results of the Raman spectroscopy measurements.

Optionally, the computer system controls the position and alignment of the ESEM autostage via an autostage alignment apparatus. The autostage is connected to the autostage alignment apparatus, whereby the autostage is moved rotationally and radially in a horizontal plane in response to computer system commands, thus aligning the selected position for the specimen with the signal producing apparatus.

Optionally, the autostage alignment apparatus includes a laser and detector for implementing a laser reflection technique, thus aligning the pharmaceutical specimen to establish an initial reference position. Optionally, the computer system stores the initial reference horizontal rotational and radial coordinates for a given specimen as a position map for a particular image.

Some scanning systems have the capability to import a position map. In the case of scanning-based systems, relatively little modification has been required to enable alignment of the scanning apparatus with the surface of a specimen because the system includes scanning hardware and software in the basic configuration of the system.

Raman spectroscopy, on the other hand, is not inherently a scanning-based measurement. Information about the composition of a sample may be obtained from a measurement at a single position, in which intensity versus wavenumber of Raman-scattered radiation is recorded. The basic configuration of a Raman spectroscopy system would therefore not necessarily include scanning hardware and software.

The modification of the present invention, wherein a Raman spectroscopy system is aligned with a selected, mapped position for a submicron chemical component using the illumination area of an ESEM is considerably greater than that required in the case of other scanning-based systems. Furthermore, Raman spectroscopy used in combination with ESEM has not been heretofore used in the pharmaceutical industry for analysis of a surface layer or the matrix of pharmaceutical specimen.

Therefore, the combination of a scanning-based system with a Raman spectroscopy system when examining such chemical components presents many challenges which the present invention addresses. Furthermore, the present apparatus is intended for use in a substantially different manner than that of other combined scanning-based systems currently known in the art, including, but not limited to, analysis using a light microscope, electron microscope or SEM in combination with a Raman or IR spectroscopy system.

In particular, the present invention provides the ability to have a submicron image with mapped positions for a given pharmaceutical specimen, to vary the depth analyzed within the matrix of the specimen using a Raman microprobe, to reproducibly position the specimen a plurality of times for analysis at a plurality of positions and provides a powerful means for quality control for the pharmaceutical industry. Comparatively, currently known scanning-analytical systems can only provide a single time-point topographical or elemental information for a specimen.

The present invention further contemplates a method for nondestructively obtaining submicron molecular data at different times on or in a surface layer or within the matrix of a single pharmaceutical specimen and for use in a variety of pharmaceutical applications and environments.

The method comprises the steps of producing an image of a pharmaceutical specimen, using the image to identify and select a position on or within the matrix of the specimen, aligning a plurality of incident radiation sources at the selected position and using a plurality of detection apparatus to detect the intensity and frequency of radiation scattered from the position, thereby obtaining the molecular composition therefrom.

The method of the present invention comprises the steps of:

i) loading a pharmaceutical specimen onto a sample plate or autostage of the apparatus as described herein (preferably, fixing the specimen onto the sample plate and orienting the sample plate on the autostage using a placement apparatus whereby the sample plate may be aligned for reproducible placement on the autostage at various times), ii) producing an image by illuminating the sample with a scanning-based system (preferably, using an ESEM), iii) using the image to map or select a position on or within the matrix of the specimen (preferably, the position map has coordinates and molecular data stored for a given position and specimen obtained at various times), iv) aligning a plurality of incident radiation sources at the selected position (wherein, preferably, at least one incident radiation source is set to a frequency chosen to provide a desired penetration depth into the specimen), v) using a plurality of detection apparatus to detect the intensity and frequency of radiation scattered from the position (preferably, the intensity and frequency shift of the scattered radiation may be compared with molecular data (either standard molecular data for a particular chemical component or molecular data previously obtained for the component at the selected position)) to obtain molecular data for the position.

The analysis may be repeated using different incident radiation sources and frequencies and other positions in order to comprehensively obtain a plurality of topographical, elemental and chemical data for a given specimen at a plurality of positions and depths. The entire procedure may be similarly repeated for other specimens.

The present invention is exemplified by application to a stability assay for a combination norelgestromin/ethinyl estradiol transdermal patch dosage form. The position of an ethinyl estradiol active drug molecule is distinguished from a norelgestromin active drug molecule and is found in the adhesive layer, within the series of patch layers. The ESEM image enables the position of the drug in the matrix to be mapped within a nanometer and its structure to be analyzed. The position and molecular data for an ethinyl estradiol active drug chemical component are thus obtained. Molecular data includes, and is not limited to, concentration ranges which, when combined with the ESEM image, allow confirmation of the presence or absence of crystalline or amorphous phases in the overall transdermal dosage form. As the process is repeated for other positions, a composition profile for ethinyl estradiol within the matrix of the transdermal patch is obtained from the occlusive backing layer through the adhesive layer to the release liner.

The present invention is further exemplified by application to a taste-mask coated tablet dosage form as a pharmaceutical specimen. Variations in coating depth are determined at a plurality of locations on the tablet and the molecular data to determine uniformity of a taste-masking agent is obtained, thus determining coating performance from lot to lot.

In these and a variety of other pharmaceutical applications intended to be included within the scope of this invention, the present invention provides a non-destructive analysis technique to compare manufacturing lots of a plurality of pharmaceutical dosage forms.

Turning to the drawings, a side elevation view of an embodiment of the apparatus recited herein for obtaining molecular data for a chemical component from a selected position on the surface of or within the matrix of a pharmaceutical specimen is shown in FIG. 1. In this embodiment, molecular data for a chemical component is obtained using Raman spectroscopy. A specimen 3 is placed on an ESEM autostage 4 and is illuminated by an incident radiation beam 2 from an ESEM 1, whereby the scattered ESEM beam 4 produces an ESEM image 5. A set of position coordinates 6 for a selected position 16 within the ESEM image 5 are derived and sent via a relay apparatus 7 to a Raman laser source 8 and to a computer system 9 (whereby the coordinates 6 are mapped to a position map 10 for the particular ESEM image 5 and stored for the particular specimen 3).

The computer system 9 generates the target map 10 by combining the coordinates 6 for each position 16 selected in the ESEM image 5. The computer system 9 also controls the operation of the apparatus of FIG. 1 including, in particular, importing a position map 10 for a particular specimen 3, aligning the Raman laser source 8 with the position coordinates 6 for a selected position 16; and, optionally, controlling an autostage alignment apparatus 11 to move the autostage 4 rotationally or radially for aligning the selected position 16 with the Raman laser source 8. Accordingly, other ESEM images 5 and positions 16 are selected and mapped by moving the position of either the Raman laser source 8 or the ESEM autostage 4.

An incident radiation beam 12 (depicted by a long-dashed line having arrows to show direction) is generated from the Raman laser source 8 (wherein the Raman laser source 8 is in a Raman microprobe configuration) and a scattered radiation beam 13 (depicted by a short-dashed line having arrows to show direction) from the position 16 is collected by a Raman collection system 14 and an intensity-wavenumber image 15 is produced. The molecular data for the position 16 is represented by the intensity-wavenumber image 15. The computer system 9 provides an output 17 by combining the position map 10 via image analysis software with the intensity-wavenumber image 15. The output 17 thus provides both the geometry and chemical bond-bond information for a plurality of positions 16 within a particular ESEM image 5 for a particular specimen 3.

The position coordinates 6 are typically 3 dimensional x-y-z coordinates for a position 16 within the ESEM image 5. Optionally, the position coordinates 6 may include other information such as the size of the area to be analyzed at the position 16. The z coordinate of the position 16 is derived from the frequency of the incident Raman beam 12 generated from the Raman laser source 8. Using a variety of sending apparatus, the relay apparatus 7 may deliver coordinates 6 from the computer system 9 to the Raman laser source 8 and, conversely, from the Raman laser source 8 to the computer system 9. Optionally, the coordinates 6 may be delivered with or without a permanent connection between the relay apparatus 7 and the Raman laser source 8 and computer system 9. The relay apparatus contemplated includes, and is not limited to, hardwiring, information storage media or radiowave. The Raman laser source 8 is preferably in a Raman microprobe configuration. The small area wherein the incident Raman beam 12 is directed, typically less than one micron, makes a microprobe configuration appropriate for analysis of many of the chemical targets found on the surface of or within the matrix of a pharmaceutical specimen. The intensity-wavenumber image 15 for the position 16 may also be compared with the intensity-wavenumber for a reference standard spectra to further and more quickly identify a chemical component at position 16.

Figure 2:
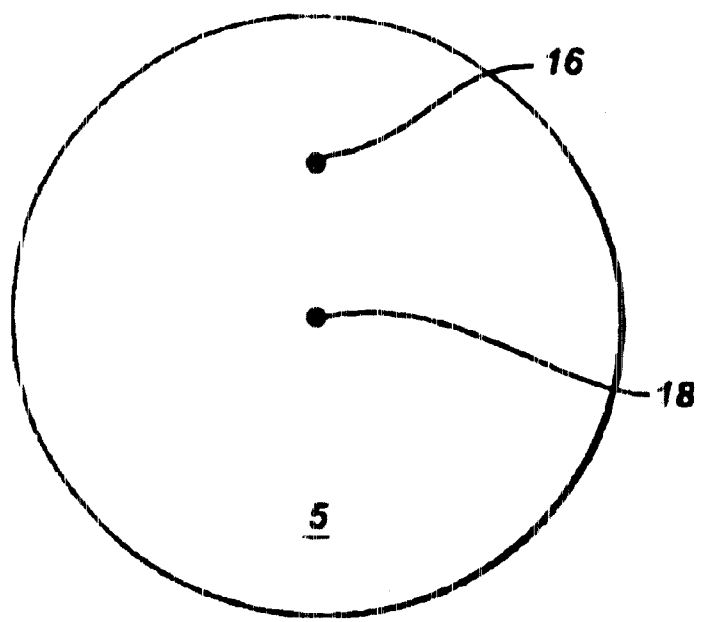
FIG. 2 is a perspective view of an embodiment of the specimen image produced by the apparatus illustrated in FIG. 1; and, FIG. 3 is a perspective view of an embodiment of the autostage illustrated in FIG. 1.

A perspective view of an embodiment of the ESEM image 5 produced by the apparatus of FIG. 1 is shown in FIG. 2. In this embodiment, a centerpoint 18 and the 2-dimensional x-y coordinates 6 of the position 16 at a distance from centerpoint 18 are algorithmically compared within the ESEM image 5 and stored in the computer system 9. Using the centerpoint 18 as a reference point, the 2-dimensional x-y coordinates 6 for other positions 16 within an ESEM image 5 may be triangulated from centerpoint 18.

Figure 3:
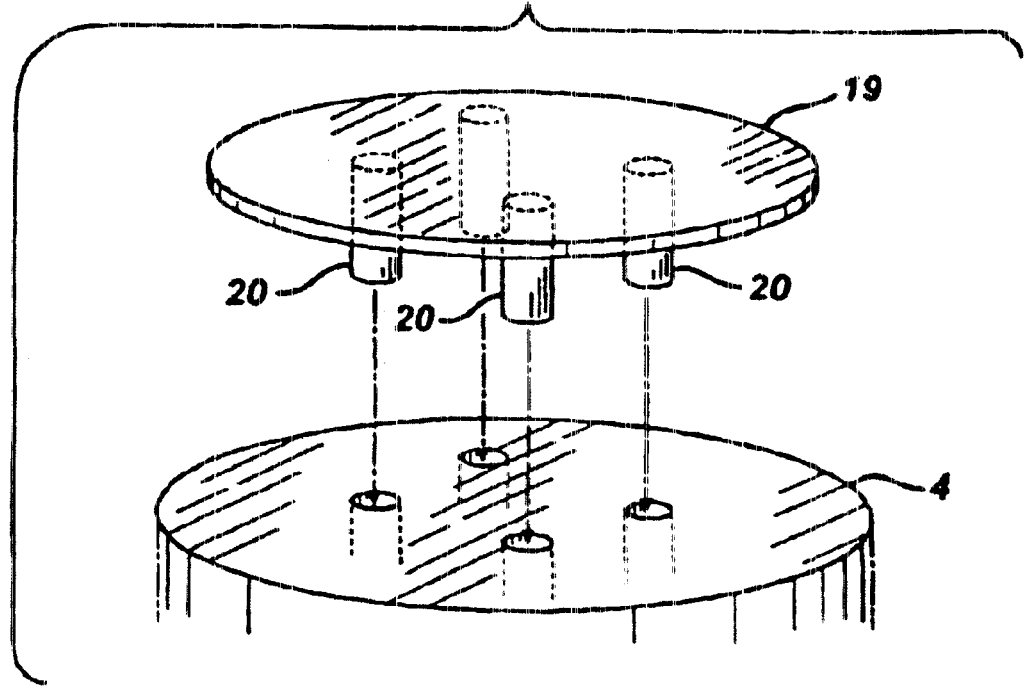

A perspective view of an embodiment of the ESEM autostage 4 included in FIG. 1 is shown in FIG. 3. In this embodiment, a sample plate 19 is removably and positionally aligned on the autostage 4 via alignment pins 20 fixed between the sample plate and the autostage.

Those skilled in the art will readily appreciate that this invention provides a method and apparatus for identifying and selecting the position of a chemical component on or in a surface layer of or in the matrix of a pharmaceutical specimen and for obtaining the nondestructive, reproducible molecular characterization thereof. Further modifications and alternative embodiments of various aspects of the invention will be apparent to those skilled in the art in view of this description. It is intended that the following claims are interpreted to embrace all such modifications and changes and, accordingly, the specification and drawings are to be regarded in an illustrative rather than a restrictive sense.

What is claimed is:

1. A method for nondestructively obtaining the molecular data for a chemical component from a pharmaceutical specimen comprising:

producing an image of a pharmaceutical specimen;

using the image to identify and select a position from which molecular data is to be obtained;

aligning a plurality of incident radiation sources at the selected position; and, using a plurality of detection apparatus to detect the intensity and frequency of radiation scattered from the position; and, thereby obtaining the molecular data therefrom.

2. The method of claim 1 wherein producing an image further comprises:

loading the specimen onto an environmental scanning electron microscope autostage; and, moving the autostage to align the specimen such that the selected position is illuminated by an incident radiation beam generated by an environmental scanning electron microscope.

3. The method of claim 2 wherein loading the specimen further comprises:

fixing the specimen onto a sample plate; and, using a placement apparatus to orient the sample plate for reproducible placement on the autostage.

4. The method of claim 3 wherein the placement apparatus comprises a combination product dependently selected from the group consisting of a sample plate on which a specimen is fixedly attached and a sample plate alignment apparatus, whereby the sample plate is removably and positionally alignable on the autostage.

5. The method of claim 3 wherein the sample plate alignment apparatus is selected from the group consisting of alignment pins fixed between the sample plate and the autostage, gridlines marked onto the autostage and gridlines debossed into the autostage.

6. The method of claim 2 wherein moving the autostage further comprises using an autostage alignment apparatus to rotationally or radially position the autostage in a horizontal plane.

7. The method of claim 1 wherein using the image to identify and select a position further comprises:

fixing a centerpoint within the image;

algorithmically determining the x-y coordinates for the position at a distance from the centerpoint;

setting the frequency of at least one incident radiation source as the z coordinate for the position; thus obtaining a set of x-y-z coordinates for a position within the image; and, using a computer system to store the coordinates for the position thus obtained.

8. The method of claim 5 further comprising obtaining a plurality of sets of x-y-z coordinates for a plurality of positions within the image; thus producing a position map for the image; and, using a computer system to store the position map thus obtained.

9. The method of claim 1 wherein the position is selected from a position on or in a surface layer or within the matrix of the specimen.

10. The method of claim 1 wherein aligning the plurality of incident radiation sources at the selected position further comprises:

using a computer system to identify and select the position from which molecular data is to be obtained;

transferring a set of position coordinates via a relay apparatus to at least one incident radiation source such that the one incident radiation source illuminates the selected position with an incident radiation beam.

11. The method of claim 1 wherein at least one incident radiation source is selected from a Raman spectroscopy system.

12. The method of claim 1 wherein at least one detection apparatus is selected from a Raman spectroscopy system.

13. The method of claim 1 wherein the intensity and frequency shift of the radiation scattered from the position is compared with a reference standard spectra to characterize the chemical components of the position.

14. The method of claim 1 further comprising nondestructively obtaining subsequent molecular data for a chemical component from a pharmaceutical specimen comprising:

selecting the image of the pharmaceutical specimen from a library of baseline images;

downloading the image into a computer system using the downloaded image to identify and select a position from which subsequent molecular data is to be obtained;

aligning a plurality of incident radiation sources at the selected position; and, using a plurality of detection apparatus to detect the intensity and frequency of radiation scattered from the position; and, thereby obtaining the subsequent molecular data therefrom.

15. The method of claim 12 wherein at least one incident radiation source is selected from a Raman spectroscopy system.

16. The method of claim 12 wherein at least one detection apparatus is selected from a Raman spectroscopy system.

17. The method of claim 13 wherein the intensity and frequency shift of the radiation scattered from the position is compared with a reference standard spectra to characterize the chemical components of the position.

18. The method of claim 1 further comprising nondestructively obtaining molecular data for a chemical component from a pharmaceutical specimen using an apparatus system comprising a combination product dependently selected from the group consisting of an imaging apparatus, a signal producing apparatus, a detecting apparatus and a mapping apparatus; whereby the combination product obtains the molecular data.

19. The method of claim 16 wherein the imaging apparatus is selected from an environmental scanning electron microscope.

20. The method of claim 16 wherein the signal producing apparatus and the detecting apparatus are independently selected from a Raman spectroscopy system.

21. The method of claim 16 wherein the mapping apparatus comprises imaging software and an integrated system for aligning a signal producing apparatus with a position on an image.

22. The method of claim 16 wherein the integrated system comprises a computer system connected to and in communication with the signal producing apparatus via a relay apparatus wherein the image and the position on the image is stored and from which the image and the position on the image is retrieved and communicated.

23. The method of claim 20 wherein the relay apparatus is selected from the group consisting of direct connection via hardwiring and indirect connection via information storage media or radiowave.

24. The method of claim 20 wherein the computer system is optionally connected to and in communication with an autostage alignment apparatus whereby an autostage is moved rotationally and radially in a horizontal plane to align the selected position for the specimen with the signal producing apparatus.

* * * * *